(12) United States Patent
Wilhelm et al.

(10) Patent No.: US 11,541,353 B2
(45) Date of Patent: Jan. 3, 2023

(54) CONTAINER AND METHOD FOR FILTERING A SUSPENSION

(71) Applicant: bbi-biotech GmbH, Berlin (DE)

(72) Inventors: Bernd-Ulrich Wilhelm, Petershagen (DE); Ulrike Klattkowsky, Berlin (DE); Jan Millauer, Berlin (DE)

(73) Assignee: bbi-biotech GmbH, Berlin (DE)

( * ) Notice: Subject to any disclaimer, the term of this patent is extended or adjusted under 35 U.S.C. 154(b) by 0 days.

(21) Appl. No.: 15/754,624

(22) PCT Filed: Aug. 25, 2016

(86) PCT No.: PCT/EP2016/070109
§ 371 (c)(1),
(2) Date: Feb. 23, 2018

(87) PCT Pub. No.: WO2017/032845
PCT Pub. Date: Mar. 2, 2017

(65) Prior Publication Data
US 2018/0243695 A1    Aug. 30, 2018

(30) Foreign Application Priority Data
Aug. 25, 2015 (DE) .................... 10 2015 216 241.9

(51) Int. Cl.
*B01D 61/18* (2006.01)
*B01D 63/02* (2006.01)
(Continued)

(52) U.S. Cl.
CPC ............. *B01D 61/18* (2013.01); *B01D 61/08* (2013.01); *B01D 63/02* (2013.01); *B01L 3/502* (2013.01);
(Continued)

(58) Field of Classification Search
CPC ................... B01D 61/18; B01D 63/02; B01D 2311/2611; B01D 2313/21;
(Continued)

(56) References Cited

U.S. PATENT DOCUMENTS 4,897,193 A    1/1990  Cais et al.
5,316,665 A *  5/1994  Hart ....................... B01D 27/06
                                                          210/316
(Continued)

FOREIGN PATENT DOCUMENTS

DE    3422435 A1    1/1986
DE    19952757 A1   5/2001
(Continued)

OTHER PUBLICATIONS

"International Application No. PCT/EP2016/070109, International Search Report dated Dec. 23, 2016", w/ English Translation, (dated Dec. 23, 2016), 7 pgs.
(Continued)

*Primary Examiner* — Madeline Gonzalez
(74) *Attorney, Agent, or Firm* — Schwegman Lundberg & Woessner, P.A.

(57) ABSTRACT

The disclosure relates to a container for filtering a suspension which comprises a lid and a vessel. The container comprises a filter that divides an interior space of the container into a first compartment and a second compartment. The lid comprises a first access and a second access. The first access is connected to the first compartment, and the second access is connected to the second compartment.

17 Claims, 16 Drawing Sheets

(51) Int. Cl.
*C12M 1/00* (2006.01)
*B01D 61/08* (2006.01)
*B01L 3/00* (2006.01)
*B01D 63/08* (2006.01)
*G01N 1/40* (2006.01)

(52) U.S. Cl.
CPC ........... *C12M 29/04* (2013.01); *B01D 63/088* (2013.01); *B01D 2311/2611* (2013.01); *B01D 2311/2615* (2013.01); *B01D 2311/2676* (2013.01); *B01D 2313/20* (2013.01); *B01D 2313/21* (2013.01); *B01L 2200/0621* (2013.01); *B01L 2200/0631* (2013.01); *B01L 2300/044* (2013.01); *B01L 2300/048* (2013.01); *B01L 2300/0681* (2013.01); *B01L 2300/0832* (2013.01); *B01L 2400/0487* (2013.01); *G01N 2001/4088* (2013.01)

(58) Field of Classification Search
CPC ............... B01D 2313/20; B01D 61/08; B01D 2311/2676; B01D 2311/2615; B01D 63/088; B01D 29/00; B01D 35/30; B01D 2201/301; B01D 2201/302; B01D 61/00; B01D 61/28; B01D 61/366; B01D 61/46; B01D 63/00; B01D 63/08; B01D 69/06; C12M 29/04; B01L 3/502; B01L 2400/0487; B01L 2300/048; B01L 2300/044; B01L 2200/0631; B01L 2200/0621; B01L 2300/0832; B01L 2300/0681; G01N 2001/4088; A61M 1/3693
USPC .. 210/767, 440, 443, 321.6, 321.72, 321.75, 210/321.84, DIG. 17, 782, 645
See application file for complete search history.

(56) References Cited

U.S. PATENT DOCUMENTS

| | | | |
|---|---|---|---|
| 5,585,007 A * | 12/1996 | Antanavich | A61L 24/106 210/500.38 |
| 5,888,831 A | 3/1999 | Gautsch | |
| 2004/0071786 A1* | 4/2004 | Grippi | A61L 24/106 424/530 |
| 2006/0060531 A1* | 3/2006 | Coville | B01L 3/502 210/650 |
| 2006/0065588 A1* | 3/2006 | Koch | B01D 53/22 210/321.88 |
| 2009/0236297 A1* | 9/2009 | Dorian | A61M 1/0204 210/782 |
| 2014/0242685 A1 | 8/2014 | Knoppke et al. | |

FOREIGN PATENT DOCUMENTS

| | | |
|---|---|---|
| DE | 10309428 A1 | 9/2004 |
| JP | 10314552 A | 12/1998 |
| WO | WO-8600704 A1 | 1/1986 |
| WO | WO-2002038503 A1 | 5/2002 |

OTHER PUBLICATIONS

"International Application No. PCT/EP2016/070109, Written Opinion dated Dec. 23, 2016", (dated Dec. 23, 2016), 7 pgs.

"International Application No. PCT/EP2016/070109, International Preliminary Report on Patentability dated Mar. 8, 2018", (dated Mar. 8, 2018), 9 pgs.

"German Application Serial No. 10 2015 216 241.9, Office Action dated Mar. 10, 2021", w/English Translation, (Mar. 10, 2021), 12 pgs.

* cited by examiner

CONTAINER AND METHOD FOR FILTERING A SUSPENSION

PRIORITY APPLICATIONS

This application is a U.S. National Stage Filing under 35 U.S.C. 371 from International Application No. PCT/EP2016/070109, filed on 25 Aug. 2016, and published as WO2017/032845 on 2 Mar. 2017, which claims the benefit of priority to German Application No. 10 2015 216 241.9, filed on 25 Aug. 2015; the benefit of priority of each of which is hereby claimed herein, and which applications and publication are hereby incorporated herein by reference in their entirety.

The invention relates to a container for filtering a suspension according to the preamble of claim 1. In addition, the invention relates to a method for accommodating and filtering a suspension.

Containers that allow a suspension to be accommodated and filtered are known from the state of the art. For example, document U.S. Pat. No. 4,897,193 shows a device composed of a mixing container, in which a mixer/separator is fitted flush and movably. At a lower end, the mixer/separator comprises a selective barrier and a channel, connected thereto, in a vertical axis. This device can be used to filter a suspension present in a mixing container. The mixer/separator is pushed into the mixing container.

As a result, the suspension is forced through the selective barrier, whereby a filtrate rises up into the channel.

It is the object of the present invention to propose a container that is suitable for filtering a suspension. Moreover, it is the object of the invention to propose a corresponding method for filtering a suspension.

This object is achieved, for example, by a container having the features of the main claim and by a method having the features of the other independent claim. Advantageous refinements will be apparent from the features of the dependent claims and of the exemplary embodiment.

The proposed container comprises a lid and a vessel. The container comprises a filter, which divides an interior space of the container into a first compartment and a second compartment. The lid comprises a first access and a second access. The first access is connected to the first compartment, and the second access is connected to the second compartment.

The accesses are typically also referred to as ports. As a result of the container comprising a first and a second access, it is achieved that a suspension can be added and withdrawn through different accesses, without the lid of the container having to be removed from the vessel in order to add a suspension or other liquid. In contrast to known containers for filtering suspensions, which necessitate opening of the container to add the suspension, in this way an introduction of undesirable particles, gases or liquids into the interior space during the addition is avoided. Additionally, it is avoided that, during the addition, microbes capable of reproduction find their way from the interior space of the container into a surrounding area of the container, and conversely from the surrounding area of the container into the interior space of the container. In this way, sterile conditions can be ensured during the addition.

The filter exhibits selective permeability and is typically configured to prevent solids present in a suspension from passing through. In general, the filter is permeable for particles up to a certain size, while it blocks particles above this particular size from passing through.

For example, when a liquid is added through the first access into the interior space, the suspension is initially located in the first compartment. Since the first compartment and the second compartment are separated from one another by the filter, a withdrawal of the liquid from the second compartment through the second access presupposes that the liquid passes through the filter. If the added liquid is a suspension having a certain average particle size, the use of a suitable filter makes it possible to achieve that the withdrawn liquid is a filtrate having a smaller average particle size or comprising no particles.

The proposed container has a simple design. Moreover, the filtration does not necessarily take place by way of a mechanical displacement of parts of the container relative to one another. A mechanical displacement, however, may be dispensed with in many embodiments. In particular for an automated filtration of a suspension using a machine, a use of the proposed container is advantageous since a filtration by way of a mechanical displacement of parts of the container relative to one another would necessitate for the machine to have a more sophisticated or more complex design, which can result in increased wear of the machine.

The container moreover allows a suspension or another liquid to be stored and transported. It is also possible to filter a suspension during the storage thereof or during the transport thereof. In addition, during filtration using the proposed container, no additional filtration device, such as a centrifuge, is required, into which the suspension or other liquid has to be transferred from a transport container for the filtration.

For example, the suspension may be a suspension comprising cells or microorganisms, such as bacteria or microscopic algae. Typically, such suspensions are cultivated in a bioreactor. Frequently, filtration of such a suspension is needed prior to analyzing the suspension, for example in a high-performance liquid chromatography system, so as to separate cells or cell debris from the liquid, for example. However, filtration may also be necessary or advantageous with other analytical methods, for example with cytometry, electrophoresis, mass spectrometry or the analysis by way of bioarray or biochip.

The proposed method is therefore advantageous for filtering a suspension. In this method, initially a container comprising a lid and a vessel is provided. The container comprises a filter, which divides an interior space of the container into a first compartment and a second compartment. The lid comprises a first access and a second access. The first access is connected to the first compartment, and the second access is connected to the second compartment. Thereafter, a liquid to be filtered is added into the interior space through the first access or through the second access, and a filtered liquid is withdrawn from the interior space through the second or the first access.

The addition and the withdrawal may take place simultaneously. If the addition and the withdrawal are carried out simultaneously, continuous filtration may take place, whereby a continuous inflow of a suspension and a continuous outflow of a filtrate take place. However, it is also possible for the addition to take place first and the withdrawal thereafter. In this way, it is also possible to store a liquid between the addition and the withdrawal. It is also possible for the addition and the withdrawal to take place simultaneously at times and separately at times.

In one embodiment, a pressure differential is applied between the first and second accesses in the method. For example, a suspension may be added into the first compartment by applying a higher pressure to the first access, and may be withdrawn from the second compartment by applying a low pressure to the second access. In this way, an increased speed of the filtration can be achieved. Moreover, no further mechanical displacement of the lid relative to the vessel is required after the lid has been mounted on the vessel.

In one embodiment, the filter is arranged in such a way that the first compartment and the second compartment are each delimited by a portion of the vessel, by a portion of the lid and by the filter. For example, the filter can be arranged centrally between the first and second accesses, and may extend from the lid to a bottom side of the vessel.

In a further embodiment, the filter is arranged in such a way that the first compartment or the second compartment is delimited only by a portion of the lid and by the filter. In this embodiment, the filter is typically attached to the lid and not in direct contact with the vessel. For example, it is possible for the filter to be arranged directly beneath the first access, so that adding a suspension into the first compartment through the first access causes the suspension to drip through the filter into the second compartment under the action of a force due to gravity, and to be filtered when passing through the filter, so that a filtrate collects at a bottom of the vessel belonging to the second compartment.

The filter may be a membrane. Depending on the type of liquid to be filtered, the membrane may comprise metal, ceramic, carbon, cellulose, glass microfibers, nylon, polypropylene, polytetrafluoroethylene, polyethersulfone or polyvinylidene fluoride, or a combination of the aforementioned materials. Additionally, the membrane may be designed as a hollow fiber membrane.

Typically, the filter includes pores having a diameter of at least 0.02 µm and/or no more than 10 µm, and preferably of at least 0.5 µm and/or no more than 3 µm. The pore size defines the size of particles that are filtered out of the suspension. A pore size between 0.02 µm and 10 µm is suitable for filtering a plurality of different suspensions containing microorganisms or cells. A size of bacteria is typically 1 µm to 10 µm. If, for example, a filter including pores that have a diameter of 0.9 µm is used, bacteria present in a suspension can thus generally be filtered out.

The interior space typically has a volume of at least 0.1 mL and/or no more than 50 mL. Such a volume of the interior space is suitable for liquid quantities typically to be filtered, transported and stored in laboratories. In particular, the volume is suitable for liquid quantities that are typically withdrawn from a bioreactor so as to analyze processes occurring in the bioreactor and conditions prevailing therein.

The vessel can be closable by the lid in a sterile manner. In this way, the lid can both prevent microbes capable of reproduction from penetrating from a surrounding area into the interior space and microbes capable of reproduction from escaping from the interior space into the surrounding area. Moreover, a contamination of samples or suspensions present in the container can thus be counteracted.

The lid and the vessel can be screwed together, for example, or connected to one another in another manner. It is also possible for the lid and the vessel to be designed to be contiguous. For example, the lid and the vessel can be produced as one piece.

Moreover, the container may be present packaged in a sterile manner prior to use.

Typically, the vessel and/or the lid comprise a thermoplastic synthetic material.

Preferably, the vessel and/or the lid are substantially made of a thermoplastic synthetic material. Typically, both the vessel and the lid are made of polypropylene. However, it is also possible for the vessel and/or the lid to be made of a thermoset material or a metal. The vessel can moreover be made of a plastic film, so that it is designed to be easily deformable and storable in a space-saving manner. As a result of the use of available materials that are inexpensive and easy to process, it is possible to achieve that the container is suitable for one-time use. A one-time use, which is to say a use of the container as a disposable item, saves a complex and energy-intensive cleaning step, which may be necessary in particular between a use of the container with differing suspensions that contain microorganisms or cells.

Typically, the first access and/or the second access comprise a septum. The suspension may be added and/or withdrawn by way of a syringe needle, for example. Accesses to the interior space can, in particular, be designed as ports comprising septa. Typically, the septa are designed so as to be piercable by a syringe needle. Additionally, the septa are typically able to re-close automatically after a syringe needle has been pulled out. The septa can be made of polypropylene or silicone, for example. The septa can be made of an elastomer.

The vessel typically has a substantially cylindrical shape. Likewise, the lid typically has a substantially cylindrical shape, so that the container has a substantially cylindrical shape. A cylindrical shape and a certain size of the vessel can be provided so that the container fits flush, to as great an extent as possible, into holders typically present on mechanical shakers, autosamplers or other feed equipment. Moreover, a cylindrical shape is also suitable in that the relative orientation of the lid with respect to the vessel need not be considered when closing or opening the vessel. Alternatively, the vessel and the lid can also have a substantially oval cross-section. A conical vessel is also possible.

Typically, the vessel comprises a rounded or a flat bottom. Moreover, the vessel typically has a height that is larger than a cross-section of the vessel.

In one embodiment, the container comprises a positioning aid, wherein the positioning aid is configured to guide the container in a defined alignment into a holder. Typically, the positioning aid is designed in the form of an outwardly directed extension, such as a pin, of the lid. The defined alignment can be achieved in that the extension engages in a groove provided on the holder. Conversely, a groove may also be provided on the lid, in which an extension provided on the holder engages. The positioning aid can also be designed in the form of a flattened side of the lid. Moreover, a positioning aid may also be provided on the vessel. This aid can be designed, for example, in the form of a flattened side of the vessel, a groove or an extension, such as a pin. The relative orientation of the lid with respect to the vessel, when the container is closed, may also be defined by a special shape of the lid and of the vessel.

A positioning aid can be advantageous when the accesses are not rotation-symmetrically arranged in the lid and, for example, are arranged next to one another on the lid. For example, if an apparatus is configured for the automated withdrawal of liquids from a container present in the holder, it may be advantageous if the accesses are always arranged in the same position relative to the holder. Appropriate positioning of the accesses can be achieved by the positioning aid.

Typically, the first access and/or the second access are suitable for treating a suspension present in the interior space by way of ultrasound. For this purpose, the accesses have a diameter of more than 1 mm, for example, so as to enable access with an ultrasonic sonotrode.

In one embodiment, the container comprises at least one pressure equalization filter, which enables pressure equalization between the first compartment and/or the second compartment and the surrounding area of the container. In one embodiment, the pressure equalization filter is provided on the lid. As an alternative, the pressure equalization filter can also be provided on the vessel. Typically, the pressure equalization filter establishes a sterile and air-permeable or gas-permeable connection between the surrounding area and the interior space of the container. For this purpose, the pressure equalization filter may be designed as a membrane and/or have an average pore size of 0.2 µm or less. In particular, the average pore size of the pressure equalization filter can range between 0.1 µm and 0.2 µm. In one embodiment, the pressure equalization filter comprises hydrophobic material, so that no larger amounts of liquid adhere thereto. In this way, reliable permeability of the filter for air or other gases can be ensured. A pressure equalization between the interior space and the surrounding area can be advantageous when adding a liquid to the container or when removing a liquid from the container. In particular, a presence of a pressure equalization filter can enable faster addition to the container.

Features of the container or of the method can be claimed combined with one another and individually.

Exemplary embodiments of the invention will be described hereafter based on the figures. In the drawings.

Figure 1:
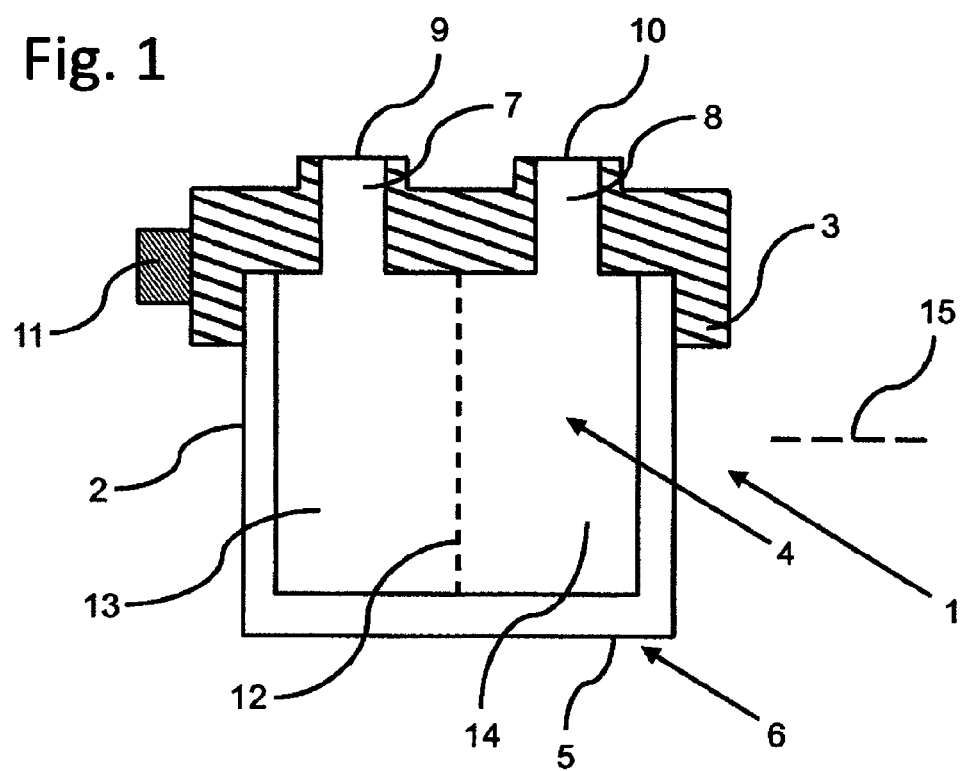
FIG. 1 shows a cross-section of a container according to a first exemplary embodiment.

FIG. 1 shows a container 1 in a first embodiment. The container comprises a vessel 2 and a lid 3. The lid 3 and the vessel 2 enclose an interior space 4 of the container 1, wherein the interior space 4 has a volume of approximately 40 mL. The vessel 2 is made of polypropylene and comprises a flat support base 5 on a bottom side 6. The lid 3 is screwed in a sterile manner onto the vessel 2 and is likewise made of polypropylene.

The lid 3 comprises a first access 7 and a second access 8, which are each designed in the form of cut-outs in the lid 3 having a round cross-section. A first septum 9 made of silicone is located on the first access 7. A second septum 10 made of polypropylene is located on the second access 8. The lid 3 additionally comprises a positioning aid 11 in the form of an outwardly directed extension.

A height of the vessel 2 is 4 cm, for example, and a radius of the round support base 5 is 2 cm, for example. The vessel 2 can have a wall thickness of less than 1 mm, for example.

Moreover, the container comprises a filter 12. The filter 12 runs vertically from the lid 3 to the bottom side 6 of the vessel 2 and divides the interior space 4 of the container into a first compartment 13 and a second compartment 14. The respective compartments 13, 14 are arranged in such a way that the first compartment 13 is connected to the first access 7, and the second compartment 14 is connected to the second access 8.

It may also be provided that the filter 12 does not extend from the bottom side 6 of the vessel 2 to the lid 3, but in one embodiment having a smaller surface area of the filter 12 extends from the bottom side 6 of the vessel 2 to a certain height in the vessel 2. In this case, the first compartment 13 and the second compartment 14 are not completely separated from one another by the filter 12, but connected to one another by an opening. Moreover, the first access 13 and the second access 14 are then connected to one another, wherein such an embodiment of the vessel 2 is suitable as long as a liquid is added to the vessel 2 only up to a fill level that is below a certain height.

The filter 12 can comprise glass microfibers, nylon, polypropylene, polytetrafluoroethylene, polyethersulfone or polyvinylidene fluoride, for example. It is also possible for the filter 12 to be a metallic filter, a ceramic filter, a carbon filter or a cellulose filter.

Figure 2:
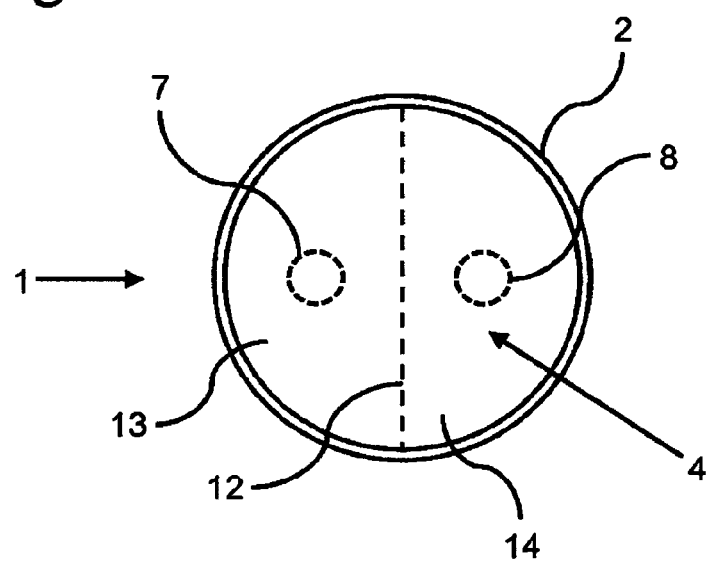
FIG. 2 shows a further cross-section of the container.

FIG. 2 shows a cross-section through the container 1 in a plane 15 extending parallel to the support base 5. Recurring features are denoted by like reference numerals in this and the following figures. The vessel 2 has a cylindrical shape, and the filter 12 divides the interior space 4 centrally, so that the first compartment 13 and the second compartment 14 each have the shape of a half cylinder. FIG. 2 moreover shows projections of the positions of accesses 7, 8 arranged above the shown cross-section.

Alternatively, in addition to a cylindrical design of the container 1, a number of different three-dimensional shapes of the container 1, and in particular of the first compartment 13 and the second compartment 14, are also possible.

Figure 3:
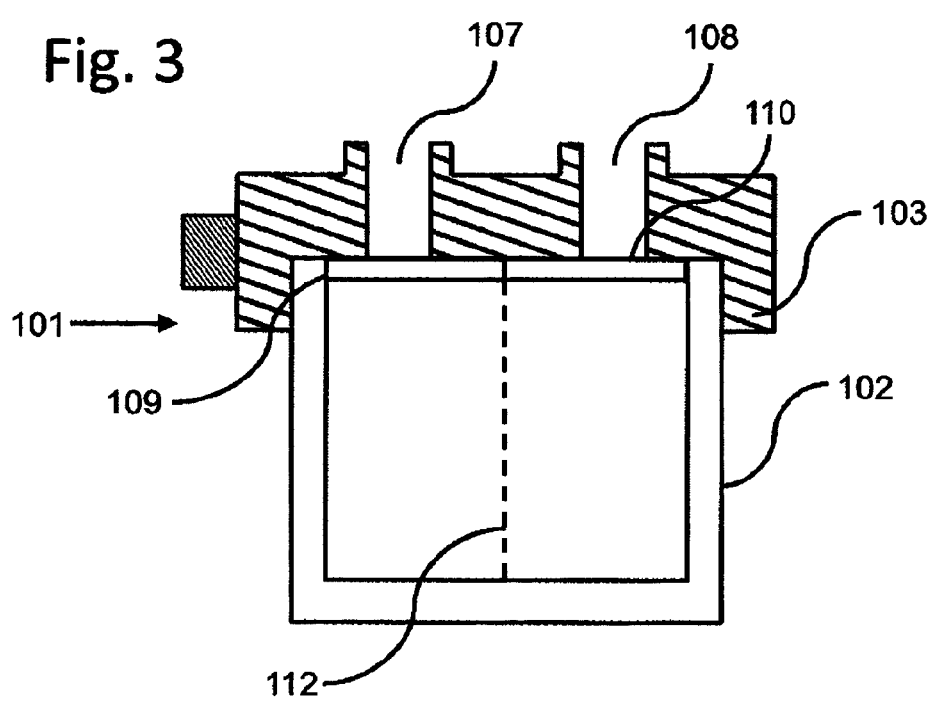
FIG. 3 shows a cross-section of a container according to a second exemplary embodiment.

A second embodiment of a container is shown in FIG. 3. Similar features in this and in subsequent figures are denoted by similar reference numerals, which is to say similar features have reference numerals increased by 100 or a multiple of 100. The container 101 again comprises a lid 103, a vessel 102 and a filter 112. In this embodiment, a first septum 109 and a second septum 110 are arranged beneath a first access 107 and a second access 108 and attached to the lid 103. The first septum 109 and the second septum 110 are not fixedly connected to one another in this exemplary embodiment. On the contrary, the septa 109, 110 can be designed so as to be individually attachable to the lid 103 by way of engagement. A one-piece design of the first septum 109 and of the second septum 110, however, is likewise possible.

Figure 4:
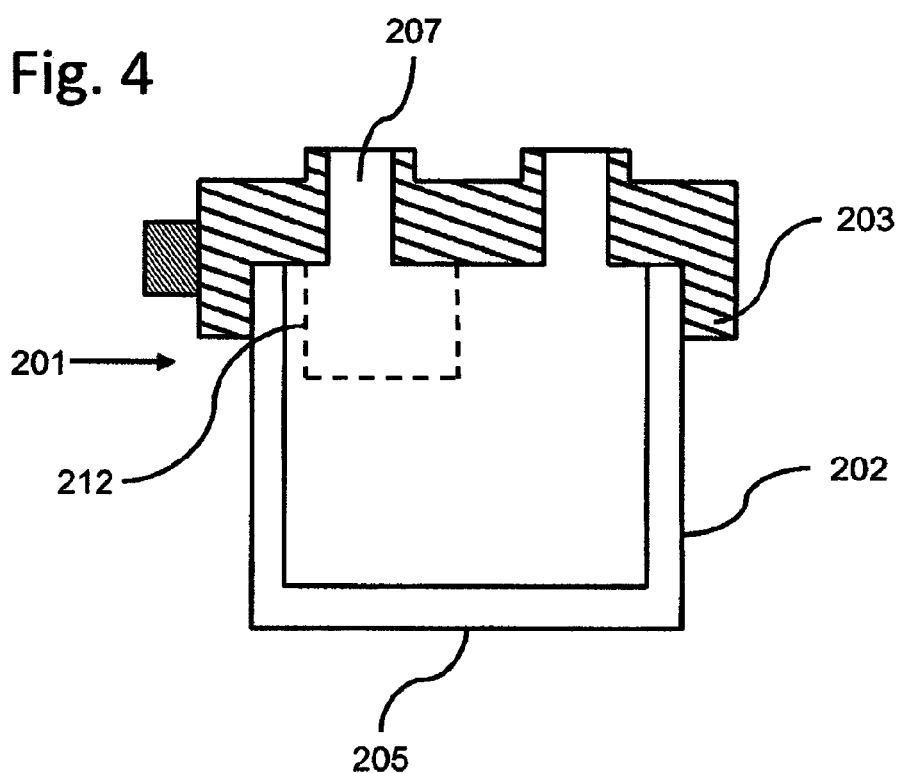
FIG. 4 shows a cross-section of a container according to a third exemplary embodiment.
Figure 5:
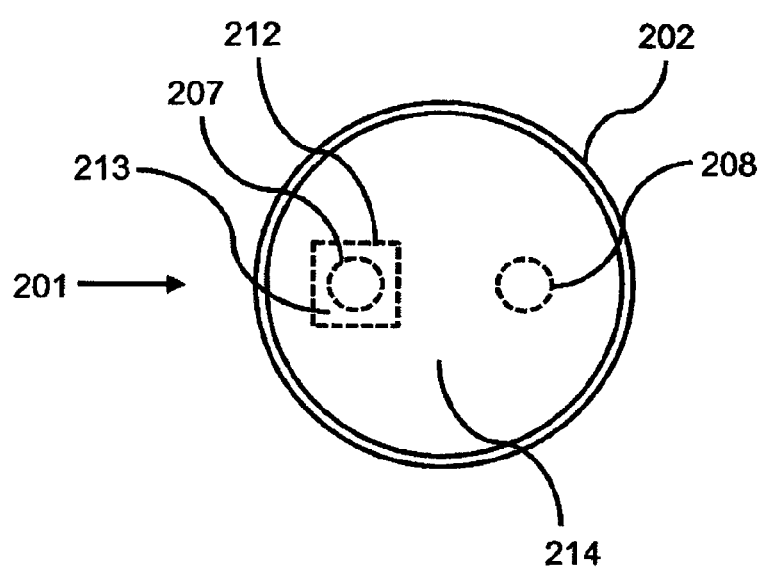
FIG. 5 shows a further cross-section of the container according to the third exemplary embodiment.

FIG. 4 shows a third embodiment of a container 201. A filter 212 is attached to a lid 203 beneath a first access 207 and has no contact region with a vessel 202. FIG. 5 shows a cross-section through the vessel 202 and the filter 212 in a plane extending in parallel to a support base 205 of the container 201. In addition, projections of the positions of accesses 207, 208 arranged above the shown cross-section are illustrated. The filter 212 has a square cross-section, so that a first compartment 213 is cubic. However, other geometric shapes of the filter 212 are also possible; for example, it can have a cylindrical, funnel-shaped or conical design. The first compartment 213 is separated by the filter 212 from a second compartment 214.

During a production of the container 1, initially the filter 12 can be attached to the lid 3 or to the vessel 2 under sterile conditions. Thereafter, the vessel 2 can be closed by the lid 3 under likewise sterile conditions. In this way, a completely sterile sub-assembly of the container 1 is provided, whereby the interior space 4 of the container 1 is present in sterile form upon delivery of the container 1. The container 1 can also be sterilized, for example, immediately before use or after use, for example by way of ethylene oxide, gamma radiation or electron radiation. Thereafter, a liquid can be added to the container 1 or a liquid can be withdrawn from the container 1 through the ports, which prevents microbes capable of reproduction from penetrating into the container 1 using suitable septa 9, 10. In this way, it is not necessary at any time to open the container 1 when the container 1 is used in a typical manner.

Figure 6:
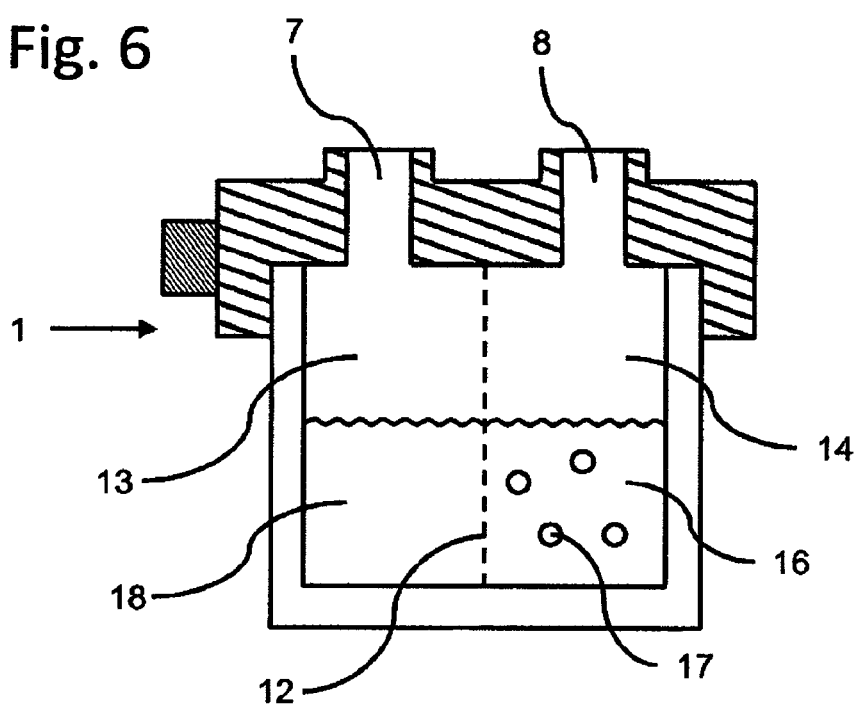
FIG. 6 shows a further cross-section of the container according to the first exemplary embodiment, a suspension, and a filtrate.

A filled container 1 in an exemplary manner according to the first exemplary embodiment is shown in FIG. 6, which is to say at a point in time after a suspension 16 was added into the second compartment 14 through the second access 8. The suspension 16 comprises a solvent and furthermore contains particles 17 having a diameter of 10 μm. The filter 12 is a membrane filter made of polypropylene and includes pores having a diameter of 1 μm. The membrane filter is permeable for the solvent, which is why a shared liquid level develops in the first compartment 13 and in the second compartment 14. Since the particles 17 are larger than the pores, the particles 17 do not make their way through the filter 12 into the first compartment 13, but remain in the second compartment 14. A filtrate 18 collects in the first compartment 13, comprising the solvent and further substances contained in the suspension 16, such as metabolic products, which have a smaller diameter than the pores or are possibly dissolved in the filtrate 18. The filtrate 18 can subsequently be withdrawn from the first compartment 13 through the first access 7, for example so as to supply this to a high-performance liquid chromatography system.

Figure 7:
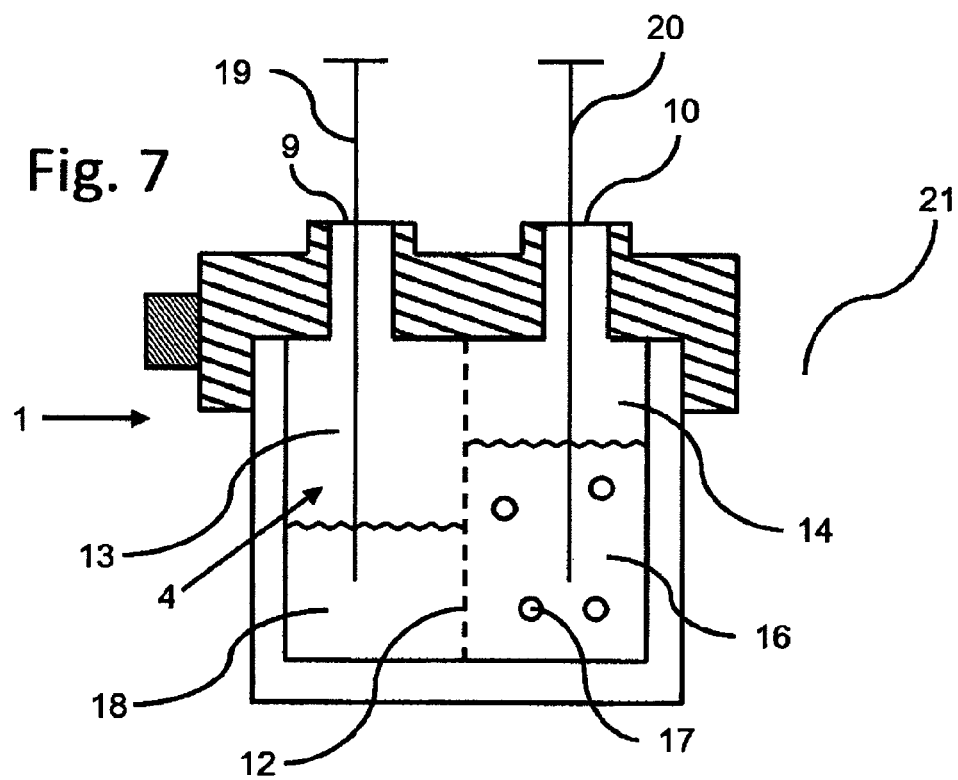
FIG. 7 shows a further cross-section of the container according to the first exemplary embodiment, a suspension, a filtrate, and a first and a second syringe needle.

FIG. 7 again shows the first embodiment of the container 1. Furthermore, a first syringe needle 19 and a second syringe needle 20 are shown. The filtrate 18 is withdrawn from the first compartment 13 through the first syringe needle 19, and a suspension 16 is added into the second compartment 14 through the second syringe needle 20. The syringe needles 19, 20 pierce the respective septa 9, 10 in such a way that the interior space 4 of the container 1 remain separated in a sterile manner from a surrounding area 21 of the container 1.

The suspension 16 is added into the second compartment 14 under a higher pressure relative to the pressure that is present in the case of a withdrawn filtrate. A sample processing machine provides a pressure differential between an addition-side suspension reservoir and a withdrawal-side filtrate reservoir.

In this example, the suspension 16 can be continuously filtered, which is to say an inflow of the suspension 16 into the container 1 and an outflow of the filtrate 18 from the container 1 take place at any point in time. However, it is also possible, for example, for the inflow of the suspension 16 and the outflow of the filtrate 18 to take place alternately. During these processes, a concentration of the particles 17 in the second compartment 14 rises steadily.

Moreover, it is possible to carry out steps that provide for a rinsing of the container 1 with a further liquid so as to remove particles 17 therefrom. For this purpose, it may also be provided that, compared to the filtration, the respective other access is used for an inflow or an outflow of a liquid.

The accesses 7, 8 typically have a round design and typically have a diameter of approximately 5 mm. However, larger diameters, for example of 10 mm, or smaller diameters are also possible. Furthermore, the first access 7 can have a diameter, for example, that differs from a diameter of the second access 8. Typically, the accesses 7, 8 are spaced apart from one another, so that the accesses 7, 8 at the same time are also easily accessible for typical syringes or other feed or withdrawal devices. Depending on the application, for example, a distance of centers of the accesses 7, 8 of 10 mm or more may represent sufficient spacing of the accesses 7, 8.

Figure 8:
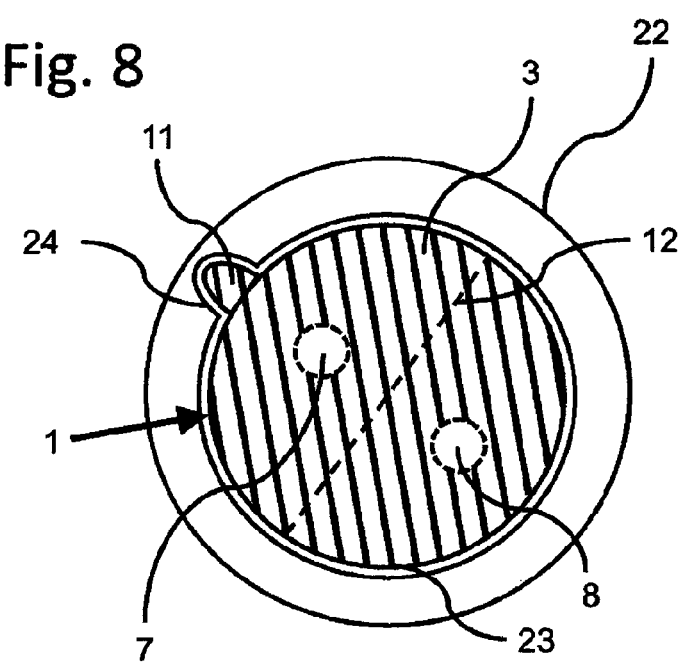
FIG. 8 shows a top view onto the container according to the first exemplary embodiment and a holder.

FIG. 8 shows a top view onto the container 1 of the first specific embodiment and a holder 22 of an autosampler. The autosampler forms part of the sample processing machine, which is configured to automatically add the suspension 16 into the container 1 and to automatically withdraw the filtrate 18 from the container 1. The first access 7 and the second access 8 are arranged next to one another in the lid 3 of the container 1. With the exception of the positioning aid 11, the lid 3 has a cylindrical outer delimiting surface 23. FIG. 8, by way of example, also shows a progression of the filter 12 arranged in the vessel 2 beneath the shown cross-section.

For the first access 7 and the second access 8 to be arranged in a defined position relative to the holder 22, a cut-out 24 is provided in the holder 22, through which the positioning aid 11 is guided during insertion of the container 1 into the holder 22, such that an alignment of the container 1 in the holder 22 is defined. The illustrated positioning aid 11 is implemented in the form of an outwardly directed extension on the lid 3. Moreover, a positioning aid 11 may additionally or exclusively be provided on the vessel 2, for example.

Likewise, it is possible for a positioning aid 11 to be implemented as a groove on the lid 3 or on the vessel 2 of the container 1. In this case, it is also possible for an indentation to be provided instead of a cut-out in the holder 22, the indentation being configured to engage in the groove on the lid 3 or on the vessel 2. Moreover, it is possible for the positioning aid 11 to be designed as a pin on the vessel 2 and/or on the lid 3. It may also be provided that the positioning aid 11 is present as a flattened side of the vessel 2 and/or of the lid 3.

Since the positioning aid 11 is provided so that the position of the accesses 7, 8 relative to a holder 22 is defined, a positioning aid 11 that is attached to the vessel 2 is particularly suited for designs in which the lid 3 has a defined alignment with respect to the vessel 2, and in particular the lid 3 should not be attached to the vessel 2 in an uncontrollably rotatable manner.

Figure 9:
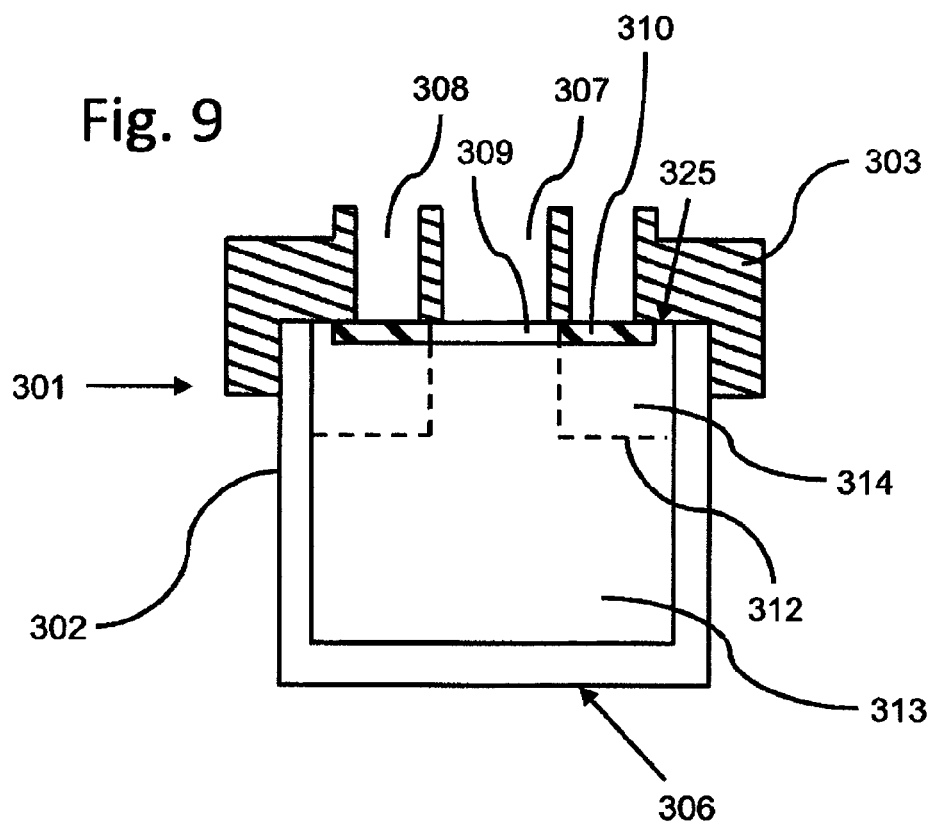
FIG. 9 shows a cross-section of the container according to a fourth exemplary embodiment.
Figure 10:
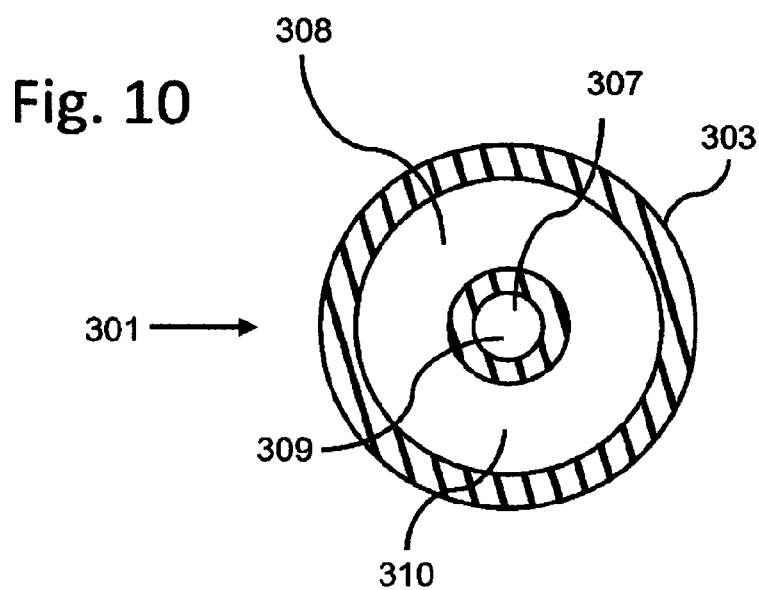
FIG. 10 shows a top view onto the container and a holder.

FIG. 9 and FIG. 10 show a fourth embodiment of a container 301. In this embodiment, a first access 307 is located centrally in the lid 303. A second access 308 is arranged in the form of a circular ring concentrically around the first access 307. A filter 312 is arranged in such a way that a first compartment 313 extends from the first access 307 to a bottom side 306 of a vessel 302. A second compartment 314 surrounds an upper region of the first compartment 313 in the form of a cylindrical ring and is arranged beneath the second access 308. On a bottom side 325 of the lid 303, the first access 307 comprises a circular first septum 309, and the second access 308 comprises a circular ring-shaped second septum 310.

In this embodiment, the container has a completely rotation-symmetrical design, for example. A positioning aid 11 is not shown in this example. However, it is possible for a rotational symmetry to be deliberately broken by a positioning aid 11 on the vessel 302 or on the lid 303.

Figure 11:
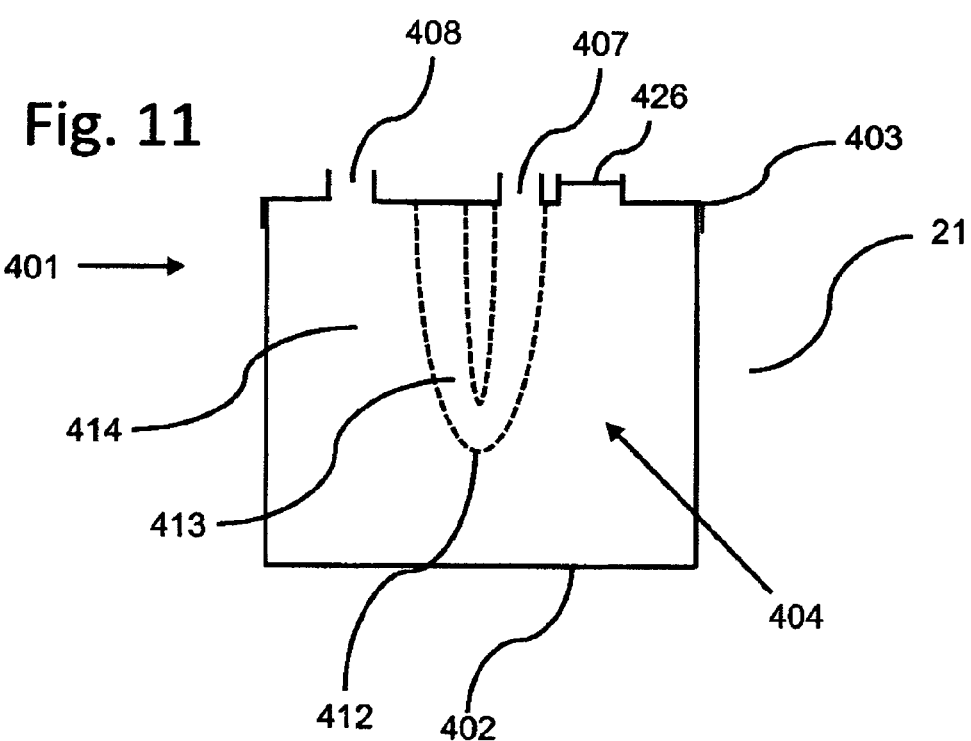
FIG. 11 shows a cross-section of a container according to a fifth exemplary embodiment.

FIG. 11 shows a further exemplary embodiment of a container 401. The container 401 differs from the containers according to the above-described exemplary embodiments in that this comprises a filter 412 in the form of a hollow fiber membrane. The filter 412 is attached to a lid 403, which in turn is connected to a vessel 402. The hollow fiber membrane comprises a cavity, which forms a first compartment 413. The first compartment 413 is attached at the lid 403 to a first access 407. A chamber outside the hollow fiber membrane forms a second compartment 414 and is connected at the lid 403 to a second access 408. The lid 403 additionally comprises a pressure equalization filter 426. This is implemented in the form of a hydrophobic membrane having an average pore size of 0.15 µm, which is fixedly connected to the lid 403, and is used for sterile pressure equalization between an interior space 404 of the container 401 and the surrounding area 21. As an alternative, the filter 412 can also be designed as a hollow fiber bundle so as to achieve a large filter surface. The hollow fiber bundle is composed of a plurality of hollow fibers, for example, which are interlaced with one another.

Such a hollow fiber bundle can be present in the interior space 404 in a variety of forms. For example, a spiral-shaped hollow fiber bundle or a ball-shaped hollow fiber bundle is possible.

Figure 12:
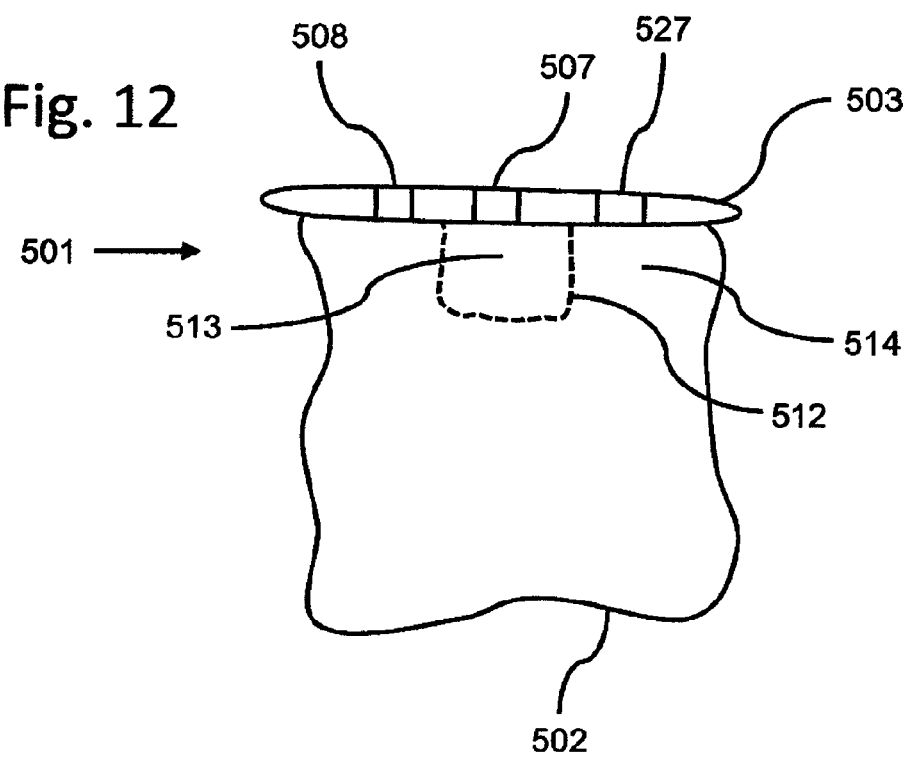
FIG. 12 shows a side view of a container according to a sixth exemplary embodiment.

FIG. 12 shows a side view of a further exemplary embodiment of a container 501 comprising a lid 503 and a vessel 502. The lid 503 is made of a thermoplastic synthetic material and connected to the vessel 502. The vessel 502 is designed in the form of a pouch made of polyethylene having a wall thickness of 0.1 mm. In this exemplary embodiment, the vessel 502 does not have a support base 5. As a result, it is possible that the vessel 502 has to be clamped into a mount, for example on the lid 503, to ensure a horizontal position of the lid 503. As is indicated in FIG. 12, the container 501 comprises a first access 507, a second access 508, a pressure equalization filter 527, and a filter 512. The filter 512 is connected to the lid 503 and divides an interior space of the container 501 into a first compartment 513 and a second compartment 514, wherein the first access 507 is connected to the first compartment 513, and the second access 508 is connected to the second compartment 514. In this example, the filter 512 is implemented as a flexible membrane. Since neither the vessel 502 nor the filter 512 is rigid, but designed to be deformable, such vessels can be stacked and stored in a space-saving manner.

Figure 13:
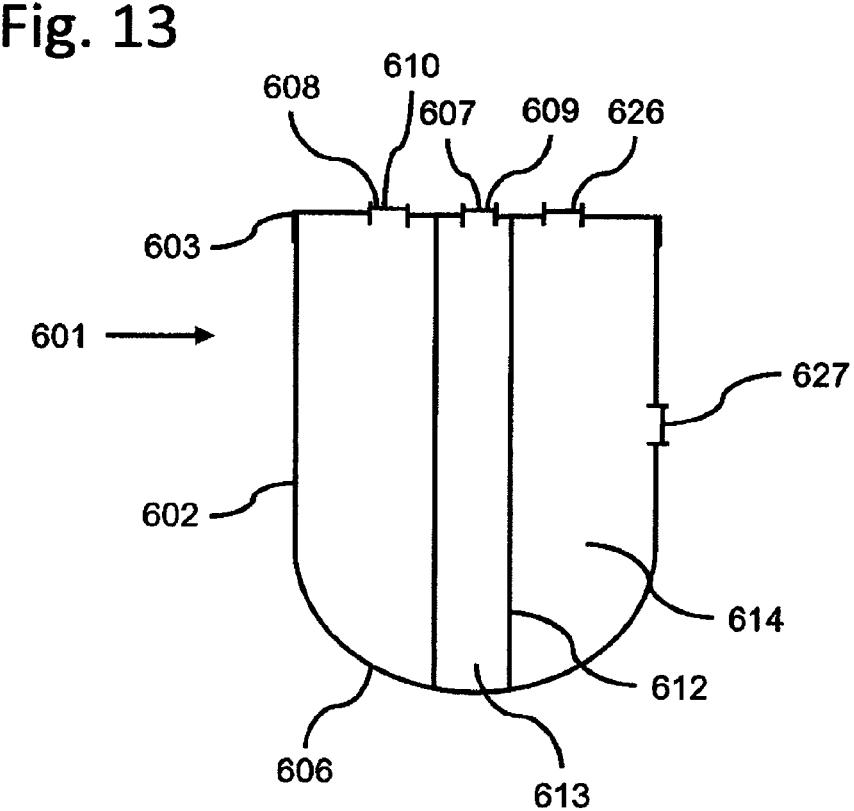
FIG. 13 shows a cross-section of a container according to a seventh exemplary embodiment.

FIG. 13 shows a cross-section of a further exemplary embodiment of a container 601. A lid 603 comprises a first access 607 and a second access 608, which comprise respective septa 609, 610, and a pressure equalization filter 626. A further pressure equalization filter 627 is provided on a vessel 602. The vessel 602 has a cylindrical shape and is rounded on the bottom side 606 thereof, making it more difficult to set the container 601 on a flat surface. A filter 612, which delimits a first compartment 613 and a second compartment 614 from one another, is designed as a concentrically arranged ceramic pipe having an average pore size of 5 µm and at a lower end is in contact with the bottom side 606 of the vessel 602.

However, it is also possible for the filter (such as the ceramic pipe) to be designed to be shorter and to be closed at a lower end, and to be arranged so as not to extend to the bottom side 606 of the vessel 602.

Figure 14:
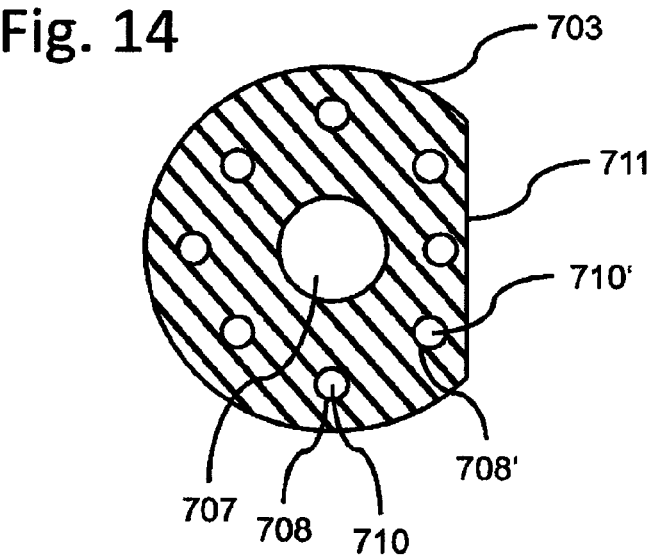
FIG. 14 shows a top view onto a lid according to a further exemplary embodiment.

FIG. 14 shows a top view onto a further exemplary embodiment of a lid 703. This has a substantially round contour and comprises a positioning aid 711 in the form of a flattened side. A first access 707 is configured for adding a suspension, has a round contour, and is arranged centrally in the lid 703. Second accesses, of which two second accesses are denoted by reference numerals 708 and 708' by way of example, having round contours and smaller diameters are arranged around the first access 707. The second accesses 708, 708' comprise respective septa, of which two septa are denoted by reference numerals 710 and 710' by way of example, and are configured for withdrawing a filtrate. However, it is also possible for a second access for withdrawing the filtrate to be arranged centrally in the lid, and for multiple first accesses for adding a suspension to the container to be arranged around this second access.

Figure 15:
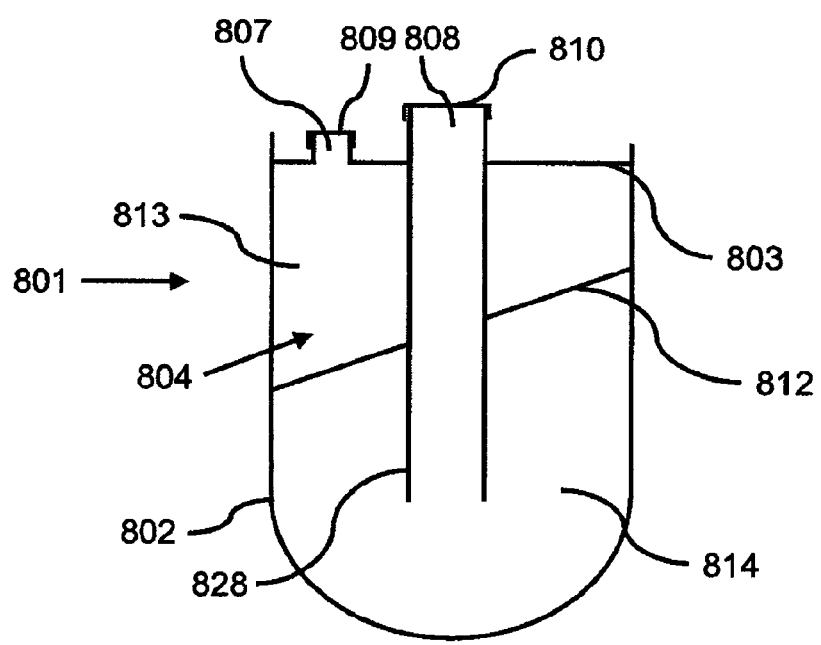
FIG. 15 shows a cross-section of a container according to an eighth exemplary embodiment.

FIG. 15 shows a further exemplary embodiment of a container 801. The container 801 comprises a lid 803 including a first access 807 and a second access 808, which comprise respective septa 809, 810. In addition, the container 801 comprises a vessel 802, in which a filter 812 designed as a membrane is obliquely fitted. The filter 812 separates an interior space 804 of the vessel 802 into a first compartment 813, which is connected to the first access 807, and a second compartment 814, which by way of a small liquid-tight pipe 828 is connected to the second access 808. The filter 812 and the small pipe 828 are designed such that an edge of a recess in the filter 812 encloses an outer side of the small pipe 828.

Figure 16:
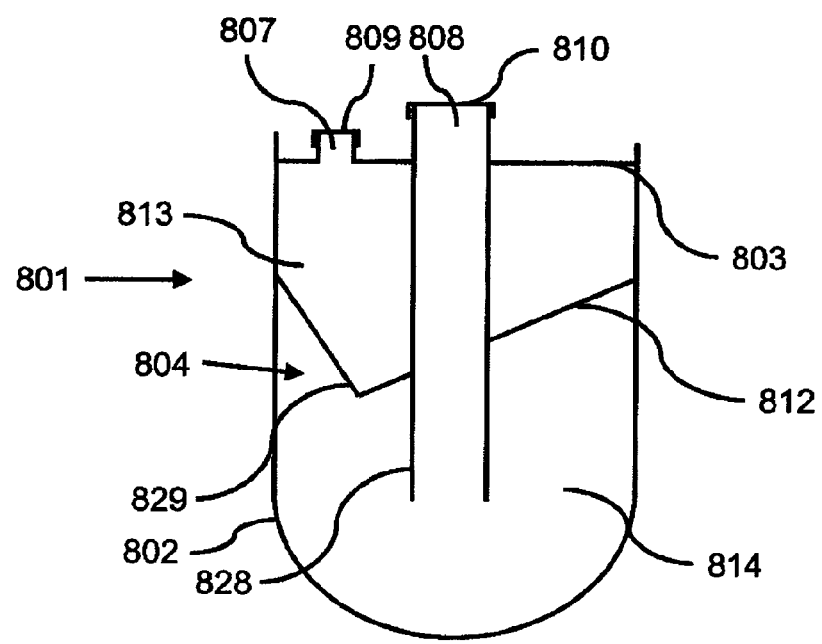
FIG. 16 shows a further cross-section of the container according to the eighth exemplary embodiment.

FIG. 16 again shows the container 801 of FIG. 15, with the difference that the filter 812 in this variant is implemented in the form of a cone. In this embodiment, the filter 812 has a lowest point 829. If the filter 812 is made of a flexible material, the lowest point 829 is not fixedly tied to one spot of the interior space 804. In this embodiment, for example, a liquid may be added into the first compartment through the first access, whereupon the liquid collects in a region close to the lowest point 829 and is also primarily filtered through the filter 812 in this region. Thereafter, the liquid can be withdrawn in filtered form through the small pipe 828 via the second access 808.

Only features of the different embodiments disclosed in the exemplary embodiments can be claimed combined with one another and individually.

The invention claimed is:

1. A container for filtering a suspension, the container comprising:
   a substantially cylindrical shaped vessel, divided into first and second compartments separated from each other by a liquid-permeable filter through which liquid can permeate between the first and second compartments, wherein the vessel has a height that is larger than a horizontal cross-section of the vessel; and
   a lid, defining a top side of the vessel, the lid comprising:
   a first septum over the first compartment, made of a material that is soft enough to be actuated open and closed automatically by respective insertion and withdrawal of a straight rigid first needle in a first direction providing a completely straight and unobstructed linear first access pathway into the first compartment;

a second septum over the second compartment, made of a material that is soft enough to be actuated open and closed automatically by respective insertion and withdrawal of a straight rigid second needle in a second direction providing a completely straight and unobstructed linear second access pathway into the second compartment; and a laterally-oriented rotational alignment positioning feature, wherein the laterally-oriented rotational alignment positioning feature aligns the first access pathway with the first compartment and aligns the second access pathway with the second compartment and is further configured to guide the container in a defined alignment into a holder, and wherein the laterally-oriented rotational alignment positioning feature is designed in the form of a laterally outwardly directed extension of the lid configured to engage in a groove provided on the holder or in the form of a groove on the lid configured to receive an extension provided on the holder, wherein the outwardly directed extension of the lid or the extension provided on the holder is a lateral pin.

2. The container according to claim 1, wherein the filter is arranged in such that the first compartment and the second compartment are each delimited by a portion of the vessel, by a portion of the lid, and by the filter.

3. The container according to claim 1, wherein the filter is arranged in such that at least one of the first compartment or the second compartment is exclusively delimited by a portion of the lid and by the filter.

4. The container according to claim 1, wherein the filter includes a membrane.

5. The container according to claim 1, wherein the filter comprises pores having a diameter of at least 0.02 µm and no more than 10 µm.

6. The container according to claim 1, wherein an interior space of the container has a volume of at least 0.1 mL and no more than 50 mL.

7. The container according to claim 6, wherein a first opening in the lid or a second opening in the lid is suitable for treating a suspension present in the interior space by way of ultra-sound.

8. The container according to claim 1, wherein the vessel is configured to be closed by the lid.

9. The container according to claim 1, wherein the vessel or the lid comprises a thermoplastic synthetic material.

10. The container according to claim 1, comprising at least one pressure equalization filter, which enables pressure equalization between the first compartment and/or the second compartment and a surrounding area of the container.

11. A method for filtering a suspension, comprising:
providing or obtaining a container, the container comprising a substantially cylindrical shaped vessel divided into a first compartment and a second compartment, wherein the first compartment and the second compartment are separated laterally from each other by a liquid-permeable filter through which liquid can permeate between the first and second compartments, wherein the vessel has a height that is larger than a horizontal cross-section of the vessel;
providing or obtaining a lid, defining a top side of the vessel the lid comprising:
a first septum over the first compartment, made of a material that is soft enough to be actuated open and closed automatically by respective insertion and withdrawal of a straight rigid first needle in a first direction providing a completely straight and unobstructed linear first access pathway into the first compartment;
a second septum over the second compartment, made of a material that is soft enough to be actuated open and closed automatically by respective insertion and withdrawal of a straight rigid second needle in a second direction providing a completely straight and unobstructed linear second access pathway into the second compartment; and
a laterally-oriented rotational alignment positioning feature, wherein the laterally-oriented rotational alignment positioning feature aligns the first access pathway with the first compartment and aligns the second access pathway with the second compartment and is further configured to guide the container in a defined alignment into a holder, and wherein the laterally-oriented rotational alignment positioning feature is designed in the form of a laterally outwardly directed extension of the lid configured to engage in a groove provided on the holder or in the form of a groove on the lid configured to receive an extension provided on the holder, wherein the outwardly directed extension of the lid or the extension provided on the holder is a lateral pin;
inserting a needle into the first septum in the first direction to introduce a fluid into the first compartment; and
inserting a needle into the second septum in the second direction to withdraw a fluid from the second compartment.

12. The method of claim 11, wherein the filter includes a membrane, wherein the filter includes multiple pores, and wherein the multiple pores have a diameter of at least 0.02 µm and no more than 10 µm.

13. The method of claim 11, wherein the vessel has a substantially cylindrical shape, and wherein at least one of the vessel or the lid comprises a thermoplastic synthetic material.

14. The method of claim 11, further comprising:
applying a pressure differential between a first opening closed by the first septum and a second opening closed by the second septum.

15. The method of claim 14, further comprising:
adding a liquid to be filtered into an interior space of the vessel through the first opening or through the second opening; and
removing a filtered liquid from the interior space of the vessel through the second opening or the first opening;
wherein the adding and the removing takes place simultaneously.

16. A system for filtering a suspension, the system comprising:
a holder; and
a container, the container comprising:
a substantially cylindrically shaped vessel, divided into a first compartment and a second compartment separated from each other by a liquid-permeable filter through which liquid can permeate between the first compartment and the second compartment, wherein the vessel has a height that is larger than a horizontal cross-section of the vessel; and
a lid defining a top side of the vessel, the lid comprising:
a first septum over the first compartment, made of a material that is soft enough to be actuated open and closed automatically by respective insertion and withdrawal of a straight rigid first needle in a first direction providing a completely straight and unobstructed linear first access pathway into the first compartment;
a second septum over the second compartment, made of a material that is soft enough to be actuated open and closed automatically by respective insertion and withdrawal of a straight rigid second needle in a second direction providing a completely straight and unobstructed linear second access pathway into the second compartment; and a laterally-oriented rotational alignment positioning feature, wherein the laterally-oriented rotational alignment positioning feature aligns the first access pathway with the first compartment and aligns the second access pathway with the second compartment and is further configured to guide the container in a defined alignment into the holder, and wherein the laterally-oriented rotational alignment positioning feature is designed in the form of a laterally outwardly directed extension of the lid configured to engage in a groove provided on the holder or in the form of a groove on the lid configured to receive an extension provided on the holder, wherein the outwardly directed extension of the lid or the extension provided on the holder is a lateral pin.

17. The system according to claim 16, wherein the filter is arranged in such that the first compartment and the second compartment are each delimited by a portion of the vessel, by a portion of the lid, and by the filter.

* * * * *